United States Patent
Hoffer

(10) Patent No.: US 7,302,296 B1
(45) Date of Patent: Nov. 27, 2007

(54) ELECTRICAL STIMULATION SYSTEM AND METHODS FOR TREATING PHANTOM LIMB PAIN AND FOR PROVIDING SENSORY FEEDBACK TO AN AMPUTEE FROM A PROSTHETIC LIMB

(75) Inventor: Joaquin Andres Hoffer, Anmore (CA)

(73) Assignee: Neurostream Technologies, Inc., Port Coquitlam (CA)

( * ) Notice: Subject to any disclaimer, the term of this patent is extended or adjusted under 35 U.S.C. 154(b) by 431 days.

(21) Appl. No.: 10/030,973

(22) PCT Filed: Jul. 5, 2000

(86) PCT No.: PCT/CA00/00789

§ 371 (c)(1),
(2), (4) Date: Jun. 3, 2002

(87) PCT Pub. No.: WO01/02054

PCT Pub. Date: Jan. 11, 2001

Related U.S. Application Data

(60) Provisional application No. 60/142,983, filed on Jul. 6, 1999.

(51) Int. Cl.
*A61N 1/34* (2006.01)
(52) U.S. Cl. .................... 607/48; 607/46; 607/49; 623/24; 623/27; 623/57
(58) Field of Classification Search ............ 607/46, 607/48–49; 623/24, 27, 57
See application file for complete search history.

(56) References Cited

U.S. PATENT DOCUMENTS

| 3,955,560 A | * | 5/1976 | Stein et al. ............. 600/377 |
| 4,232,679 A | | 11/1980 | Schulman |
| 5,314,495 A | * | 5/1994 | Kovacs ..................... 623/25 |
| 5,413,611 A | | 5/1995 | Haslam |
| 5,824,027 A | | 10/1998 | Chen |
| 5,851,223 A | | 12/1998 | Litvinov |

FOREIGN PATENT DOCUMENTS

WO    WO 9825552    6/1998

OTHER PUBLICATIONS

"Strategies for providing upper extremity amputees with tactile and hand position feedback," Riso, available in "Proceedings of the International Biomechatronics Workshop" on Apr. 1999.*
"Afferent Sensory Feedback for Lower Extremity Prosthesis," Clippinger et al., Sep. 1982.*
"Discrimination of Phantom Hand Sensations Elicited by Afferent Electrical Nerve Stimulation in Below-Elbow Amputees," Anani et al., Med. Progr. Technol. 6, 131-135 (1979).*

* cited by examiner

*Primary Examiner*—Carl Layno
*Assistant Examiner*—Shevon E Johnson
(74) *Attorney, Agent, or Firm*—Seyfarth Shaw LLP

(57) ABSTRACT

This invention relates to a system and methods for relieving phantomlimb pain in amputees, and for providing an amputee with sensory feedback from a prosthetic limb. The system employs implantable multichannel, multi-chambered interface structures, namely, nerve cuffs. The implanted nerve cuffs have electrodes which transmit electrical signals generated by a signal generator to nerves, recruiting certain neurons to send sensory signals to the cerebral cortex, suggesting sensory sensations to the amputee. Such signals can arise directly from the signal generator, approximating the train of signals seen by the cortex in a normally innervated limb, or can originate from sensors in a prosthetic limb.

49 Claims, 3 Drawing Sheets

ELECTRICAL STIMULATION SYSTEM AND METHODS FOR TREATING PHANTOM LIMB PAIN AND FOR PROVIDING SENSORY FEEDBACK TO AN AMPUTEE FROM A PROSTHETIC LIMB

PRIORITY CLAIM

This application is a §371 U.S. national stage of PCT/CA00/00789 filed Jul. 5, 2000, which was published in English under PCT Article 21(2), which in turn claims the benefit of U.S. Provisional Application 60/142,983 filed Jul. 6, 1999.

TECHNICAL FIELD

This invention relates to a system and methods for electrical stimulation of body tissues, and more particularly to a system and methods for stimulating nerves to alleviate phantom limb pain in an amputee, and/or for providing sensory feedback from a prosthetic limb worn by an amputee.

BACKGROUND

Limb amputations cause three major types of dysfunction. Two of these occur immediately, and are direct consequences of the amputation, the loss of motor function below the amputation level; and the loss of all sensory feedback arising from the missing limb below the amputation level.

The third, more indirect dysfunctional consequence of amputation is that which is known as "phantom limb" sensations. These may occur either soon after, or at various delayed times after amputation. An amputee having such sensations may still "feel" his or her amputated limb in place. Of particular concern is phantom limb pain, where the amputee feels sensations of pain seemingly arising from the original limb The causes for the often very vivid and disturbing phantom limb sensations reported by a majority of limb amputees are not completely understood, but it is believed that several processes are responsible Subsequent to loss of normal peripheral sensory nerve input, neurons in regions of the cerebral cortex and in particular in the primary sensory cortex associated with the amputated limb can greatly increase their receptivity to synaptic inputs arising from the sensory nerves that remain in the limb stump but are now disconnected from their sensory end-organs.

Cortical neurons can also become more receptive to sensory input arising from other regions of the body, in particular from regions that normally project to areas of cortex adjacent to the cortical areas originally dedicated to the amputated limb or body parts. This cortical response process, described as "cortical plasticity" (Ramachandran, V. S., and Hirstein, W. (1998). *The Perception of Phantom Limbs*. The D. O. Hebb lecture. Brain 121: 1603-1630), can manifest itself as early as 2 hours after experimental digit nerve amputation in animal models (Merzenich M M, Kaas J H, Wall J T, Sur M, Nelson R J, Felleman D J. (1983) *Progression of Change Following Median Nerve Section in the Cortical Representation of the Hand in Areas 3b and 1 in Adult Owl and Squirrel Monkeys*. Neuroscience 10(3): 639-65); (Kaas J H. (1998) *Phantoms of the Brain*. Nature 391(6665):331, 333) and continues to develop for many weeks and months if peripheral nerves remain transected and cannot reestablish contact with their original or other suitable target organs.

It is believed that this greatly increased responsiveness of cortical neurons to inappropriate sensory inputs is at least partly responsible for phantom limb sensations. Phantom limb sensations are thus interpreted to arise from the missing limb or digits, even though the sensations may be triggered by sensory receptors from other body regions or by random activity in the disconnected sensory endings within the amputated limb stump.

Such phantom limb sensations may or may not include pain components. When pain is present, it is sometimes of such intensity that it becomes unbearable or extremely disabling to the amputee. One possibility which may account for the occurrence of phantom limb pain is that amputation eliminates or greatly disrupts the normal flow of sensory information arising from other modalities of sensory receptors (e.g., low-threshold cutaneous or muscle receptors) carried by larger diameter, myelinated axons. These sensory axons normally-convey non-painful information of proprioceptive and cutaneous origin such as touch, pressure, temperature, muscle length, tendon force or joint position.

An important landmark in the pain scientific literature is the work by Wall and Melzack ((1965) *Pain Mechanisms: A New Theory*. Science 150(699):971-9), who in the 1960's proposed the "Gate Control Theory" of pain whereby activity in large diameter touch Ab nerve fibers were hypothesized to reduce the central transmission of pain activity information carried to the spinal cord by smaller A$\delta$ and C fibers. Although this hypothesis remains controversial, it has brought a focus on the complex interactions that can exist among parallel sensory inputs of different modalities, and on the various central and peripheral factors that can contribute to the central perception of pain. It is now generally accepted that the balance of activity in large and small diameter sensory nerve fibers is important in pain transmission in the spinal cord and brain centers.

In one theory of synaptic connectivity in the central nervous system, proposed by Wall and Melzack, synaptic input from large myelinated sensory fibers normally converge on interneurons that mediate pain pathway information and tend to inhibit the transmission of pain sensations that are conducted by smaller diameter, unmyelinated sensory nerve fibers. In the absence of proprioceptive and cutaneous information that could inhibit the transmission of pain, the pain pathways are open. The sensations of pain that reach the cortex are interpreted to arise from the missing limb or digits (thus the term "phantom limb" pain), even though the sensations may be triggered by sensory receptors from other body regions, or by random activity in pain afferents in the nerve stumps in the amputated limb or digits.

With respect to the fate of nerve fibers in amputated limbs, it is known that all nerve fibers in a severed nerve may atrophy to some extent in the sense that the fiber diameters are reduced, but the nerve cells generally remain viable in the sense that they continue to conduct electrical impulses and retain their basic synaptic connectivity patterns. It is also known that sensory fibers atrophy relatively more than motor fibers (Hoffer, J. A., Stein, R. B. and Gordon, T. (1979) *Differential Atrophy of Sensory and Motor Fibers Following Section of Cat Peripheral Nerves*. Brain Res. 178:347-361) and, furthermore, that large-diameter sensory fibers typically atrophy more than small-diameter sensory fibers. Similarly, large-diameter motor fibers typically atrophy more than small-diameter motor fibers. For hind limb nerves of cats that were cut and ligated over a period of 300 days, Milner et al. ((1981) *The Effects of Axotomy on the Condition of Action Potentials in Peripheral Sensory and Motor Nerve Fibres*. J Neurol Neurosurg Psychiatry 44(6):

485-96) found that large sensory fibers had a 60% decrease in conduction velocity (CV); small sensory fibers had about a 45% decrease in CV; large motor fibers had about a 40% decrease in CV: and small motor fibers had about a 20% decrease in CV. Thus, in amputated nerves, "large" and "small" nerve fibers will gradually become closer in their diameters and consequently closer in their thresholds for electrical stimulation.

DESCRIPTION OF PRIOR ART

Various pharmacological approaches have been proposed for treating phantom limb pain. Analgesics have generally not worked against this kind of pain. Antidepressant medications can reduce the sensation of pain, but have serious side effects that have limited their applicability There are currently no approved drugs that are recognized to treat phantom limb pain safely and effectively without unwanted side effects. Another approach, the blockade or removal of the sympathetic supply to the stump, can provide temporary reduction of phantom pain but the effects depend on how soon after amputation the procedure is done, and may not be long-lasting (Livingston KE (1945) *Phantom Limb Syndrome. A Discussion of the Role of Major Peripheral Nerve Neuromas*. J. Neurosurgery 2:251-5).

It is known that electrical stimulation of nervous structures can be effective in providing relief of certain types of peripheral pain. Two main approaches used to date are transcutaneous electrical nerve stimulation (TENS) and dorsal column stimulation (DCS) in the spinal cord. It is likely that the mode of action of these therapies involves the stimulation of large diameter sensory fibers in limb nerves (TENS) or in the spinal cord (DCS), reducing the transmission of pain in central pathways described by the Gate Control Theory.

However, application of these electrical stimulation techniques has had only modest success for treatment of phantom limb pain in amputees. It is likely that TENS ceases to be effective as the sensory fibers in amputated nerves become gradually thinner. As they do so, their electrical thresholds gradually rise, to the point that the fibers can no longer be recruited effectively with TENS.

There is some limited evidence that it is possible to selectively stimulate large-diameter sensory fibers in severed nerves of amputees by providing electrical stimulation, thereby eliciting touch sensations without causing any concomitant pain sensations. Stein, R. B., Charles, D., Hoffer, J. A., Arsenault, J., Davis, L. A., Moorman, S. and Moss, B. (1980) *New Approaches to Controlling Powered Arm Prostheses, Particularly by High-Level Amputees*. Bull. Prosth. Res. 17:51-62, showed that it is possible to elicit sensations that the amputee interpreted to arise from an amputated limb, by electrically stimulating sensory axons in a ligated peripheral nerve inside the forearm stump of a below-elbow arm amputee. Even though the arm had been amputated over 30 years earlier, the amputee subject was able to clearly sense the stimulation, which he reported as a non-noxious tingling sensation arising from the ulnar aspect of his phantom limb, specifically from the ring and small fingers which is the sensory field that is normally innervated by the ulnar nerve. The amputee was able to subjectively discriminate frequencies of stimulation ranging from single pulses to steady rates up to 10-20 Hz. For frequencies greater than 20 Hz the sensations were reported as either fused or absent, indicating that the nerve fibers could have been fatigued by high-frequency stimulation in this patient. This reference suggests that severed sensory nerve fibers in amputees can survive for 30 years or longer in the absence of suitable connections to sensory end-organs.

Sculman (U.S. Pat. No. 4,232,679) and Schwabe (WO 98/25552) describe systems for providing stimuli to human tissues, but do not have the advantages provided by the present invention.

SUMMARY OF INVENTION

This invention provides a system and methods for alleviating phantom limb pain and for replacing lost sensory function from a missing limb.

Activity flowing centrally along larger diameter sensory fibers can help suppress the central perception of pain information carried by smaller diameter fibers and, as a corollary, when there is an absence of activity that would normally occur in large diameter sensory fibers, such as in touch receptor afferents that have been disconnected from their peripheral sensory organs, there is a greater chance for pain sensations to reach consciousness. This condition, when it occurs in amputees, for example, may be reversed by selective electrical stimulation of the larger sensory fibers to so restore sensory traffic in these fibers, thus restoring a more normal balance of activity in large and small diameter fibers which will counterbalance again the excessive flow of pain information in central pathways Specifically, the invention provides a system for alleviating phantom limb pain which has an implanted electrode or electrodes located in, around or near the severed peripheral nerve stumps that remain inside the proximal stump of an amputated limb Appropriately chosen electrical stimulation parameters can accomplish the following desirable purposes 1) provide sensory feedback about parameters of a prosthetic limb, such as touch, pressure, force, slip, joint position or temperature information; and/or
2) provide an effective method of treatment of phantom limb pain.

More specifically, the invention provides a system for alleviating phantom limb pain in an amputee having a limb stump, the system comprising a plurality of electrodes implanted in the limb stump, the electrodes placed in close proximity to a severed sensory nerve in the amputee's limb stump, the electrodes when supplied with electrical current providing electrical stimulation to said nerve; and an electrical signal generator fashioned to communicate varying electrical signals to each electrode in a preferred embodiment, the electrodes are incorporated within a tubular nerve cuff fashioned to be implanted in the limb stump so as to circumferentially surround a portion of the nerve.

In a further embodiment nerve cuff is multi-chambered, and each of the electrodes is segregated into one chamber of the nerve cuff, each electrode thereby being placed in close proximity to a different portion of the nerve.

Alternatively, one or more catheters can provide selective delivery of pharmacological agents to the nerve stumps for the treatment of pain In one embodiment, the invention has in particular multi-channel interface structures, which may be implanted to permit stimulation of multiple sites or sensory modalities of internal body tissues, such as nerves, together with selective infusion of chemical substances. The interfaces may be provided in the form of nerve cuffs. The interfaces may provide electrical, chemical and/or optical connections to selected bodily tissues.

Preferred embodiments of the invention increase the effectiveness of selective recruitment with electrical stimulation of large sensory nerve fibers in severed nerve stumps in amputated limbs by providing electrodes which are implanted inside the amputated limb, directly on or very close to the nerve stumps. Because nerve fibers of different diameters atrophy differently, the thresholds for electrical stimulation of large and small sensory fibers tend to gradually move closer together. Placing the stimulating electrodes closer to the nerve provides an improved means for selectively stimulating the large fibers even after they have atrophied as a consequence of the nerve amputation.

More specifically, the invention provides a system for alleviating phantom limb pain in an amputee having a limb stump, the system comprising a plurality of electrodes implanted in the limb stump, the electrodes placed in close proximity to a severed sensory nerve in the amputee's limb stump the electrodes when supplied with electrical current providing electrical stimulation to said nerve, and an electrical signal generator fashioned to communicate varying electrical signals to each electrode in a preferred embodiment, the electrodes are incorporated within a tubular nerve cuff fashioned to be implanted in the limb stump so as to circumferentially surround a portion of the nerve.

In a further embodiment, nerve cuff is multi-chambered, and each of the electrodes is segregated into one chamber of the nerve cuff, each electrode thereby being placed in close proximity to a different portion of the nerve. Cuff electrodes are considered to be easier to install and more efficient than other types of electrodes for providing the desired stimulation. Multichannel electrodes are also more efficient for selectively recruiting desired sensory nerve modalities with electrical stimulation. Multi-chambered nerve cuffs are the most preferred design for providing multichannel stimulation.

Another aspect of this invention provides methods of application of non-noxious electrical stimulation of larger, lower-threshold myelinated sensory axons in severed nerve stumps, which may serve to disfacilitate or inhibit the transmission of pain sensations in central pathways. These methods of stimulation may also act to arrest or reduce the evolution of synaptic changes that are believed to occur in the sensory cortex after limb amputation that may be responsible for "phantom limb" sensations, and in particular phantom limb pain sensations.

BRIEF DESCRIPTION OF DRAWINGS

In drawings which illustrate one particular embodiment of the invention.

DESCRIPTION

Figure 1:
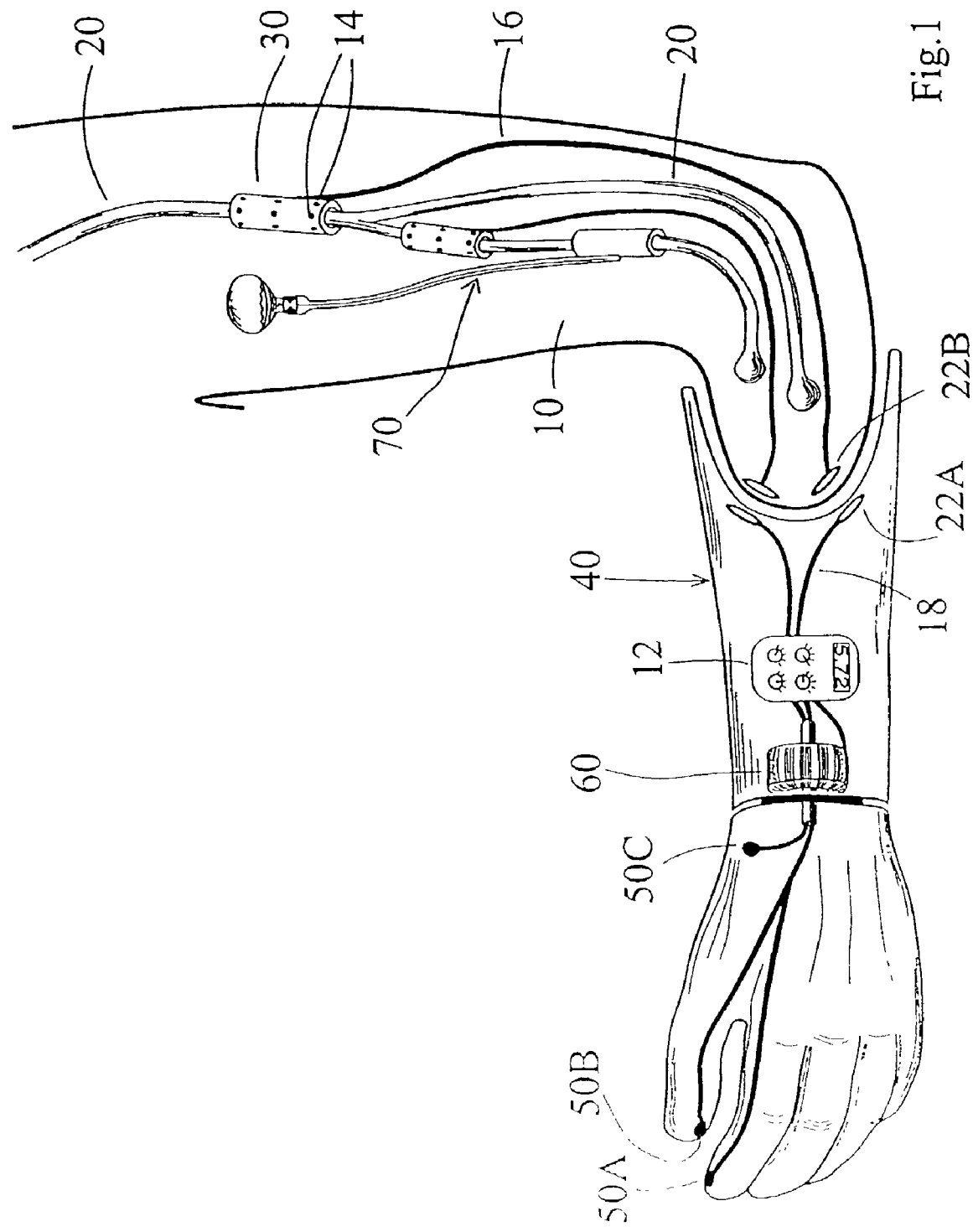
FIG. 1 is a schematic view of an amputee's limb stump and a prosthetic limb equipped with a system for alleviating phantom limb pain and for practising the methods of the invention; and, FIGS. 2 and 3 are respectively perspective and cross sectional views of a multi-channel nerve-cuff surrounding a ligated severed nerve in an amputee's stump

As shown in FIG. 1, the present system for alleviating phantom limb pain in an amputee having a limb stump 10 has a plurality of electrodes 14 (shown in greater detail in FIGS. 2 and 3) implanted in the limb stump 10, in close proximity to a severed afferent or "sensory" nerve 20 in limb stump 10, which nerve 20 had innervated the amputated limb.

Fashioned to communicate electrical signals to electrodes 14 is an electrical stimulation system south as electrical signal generator 12. Signal generator 12 may be implanted in limb stump 10 and connected directly to electrodes 14 by suitable biocompatible cabling (not shown), or, as shown in FIG. 1, signal generator 12 may be outside of the amputee's body In this instance signals communicated by signal generator 12 to electrodes 14 are preferably transmitted telemetrically in part to avoid having cabling pass through the amputee's skin. As shown in FIG. 1, in the preferred embodiment of the invention signals from signal generator 12 may pass through external cable 18 to transmitting antenna 22A, across the skin of the amputee to receiver antenna 22B, and then through cable 16 to electrodes 14.

Figure 2:
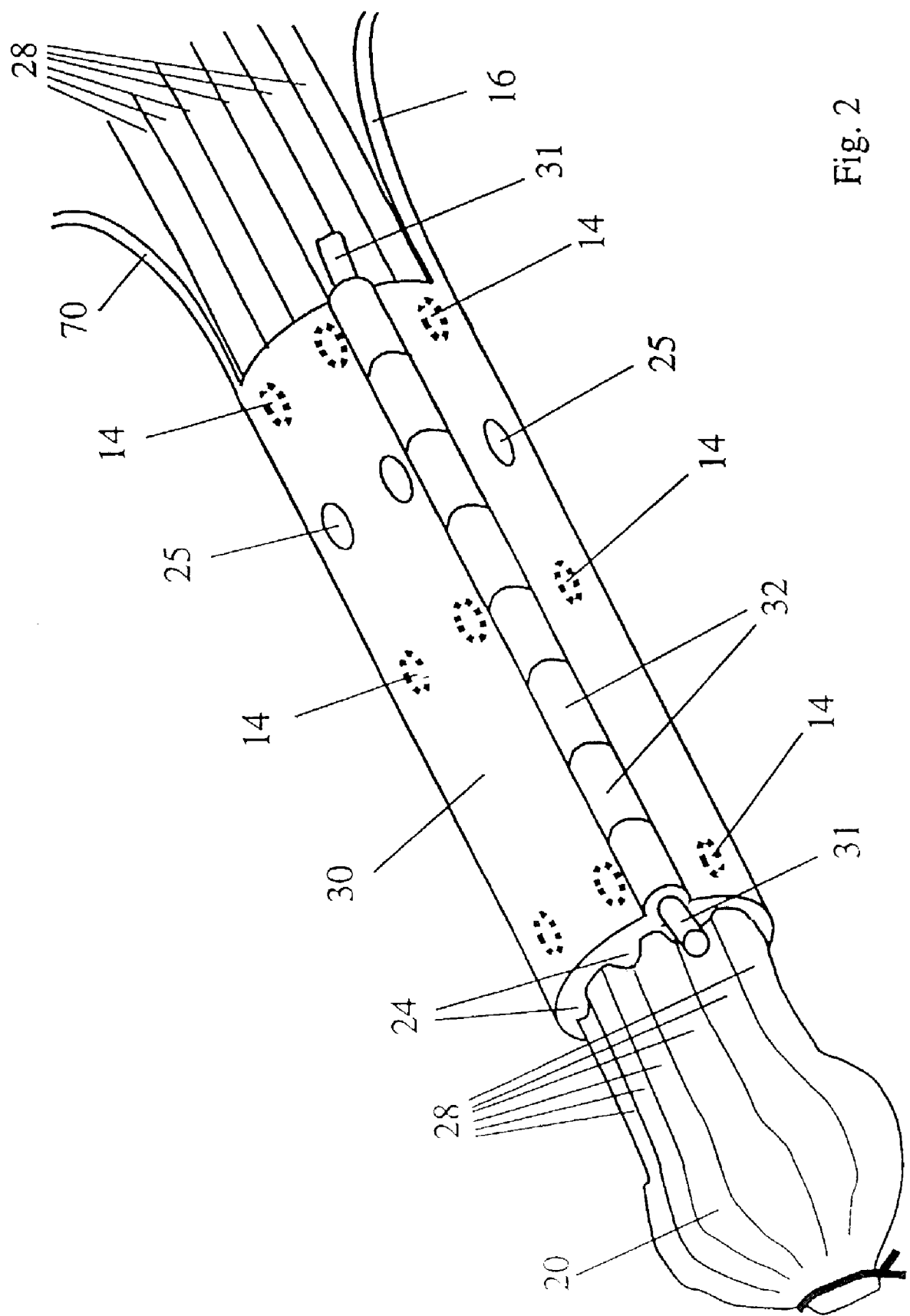
Figure 3:
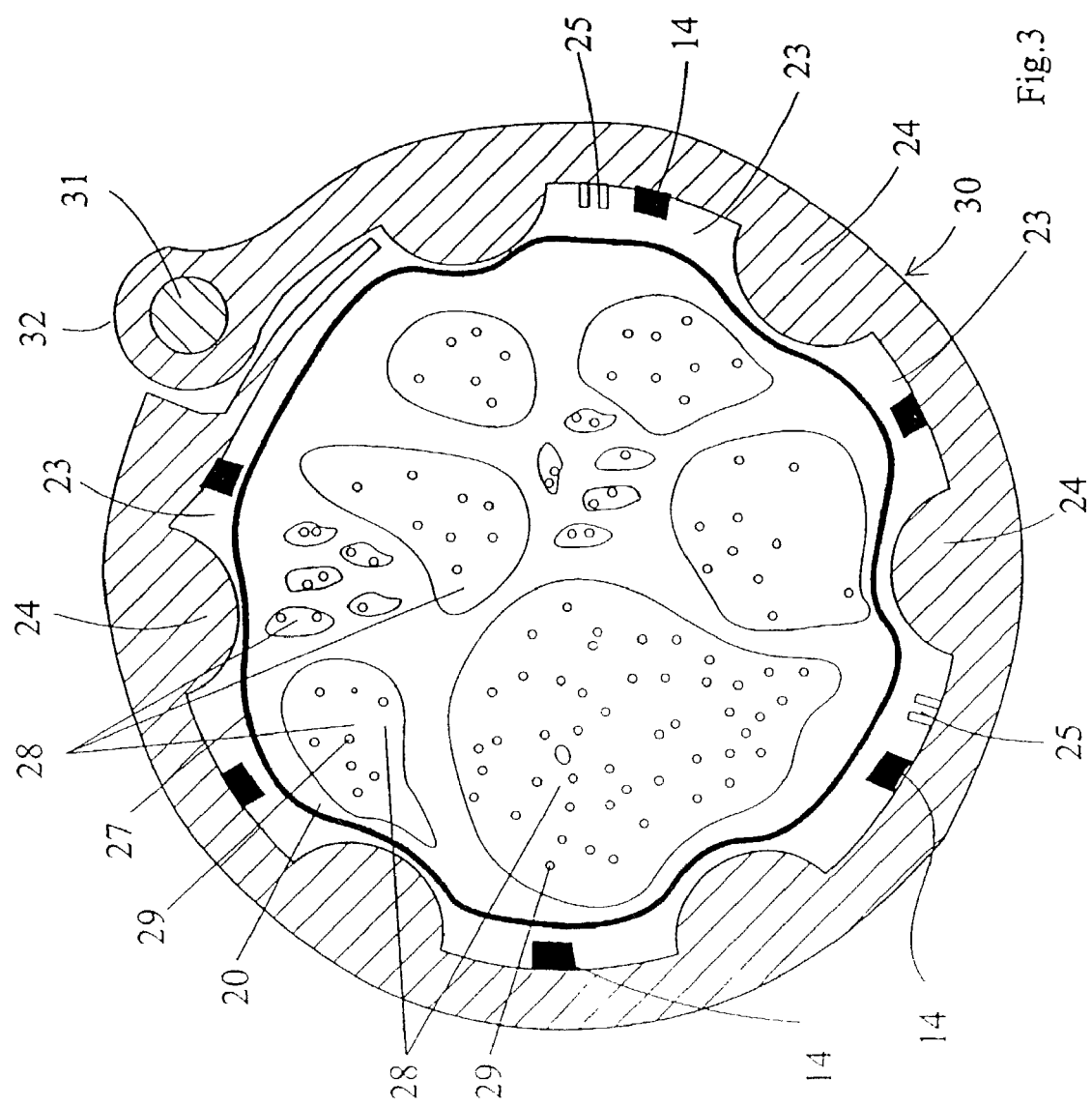

As discussed above, each electrode 14 is implanted in limb stump 10 in close proximity to nerve 20. As shown in FIGS. 2 and 3, nerve 20 may comprise a plurality of nerve fascicles 28 and individual nerve axons 29, all encompassed within the perineurium 27.

It has been determined that electrical signals provided by electrodes 14 to nerve 20 will stimulate or recruit certain portions of nerve 20 (ie. certain neurons), to provide nervous signals, in the form of action potentials, therein. In the context of the description herein, "in close proximity to nerve 20" means that electrodes 14 are implanted in close enough spaced relation to nerve 20 to cause signals to be produced in nerve 20 by transmission of the electrical signals produced by signal generator 12. Accordingly, electrodes 14 may be implanted directly in nerve 20, but may also rest directly on the surface of nerve 20, or may be some small distance away from the surface of nerve 20, as long as the transmission, by electrodes 14, of signals produced by signal generator 12 still causes nervous signals in the form of action potentials to be produced in, and conducted along, nerve 20

In a preferred embodiment of the present invention, the electrodes 14 of the system are incorporated within a nerve cuff 30 fashioned to circumferentially surround the nerve 20 when implanted. Such a nerve cuff 30 is shown in greater detail in FIGS. 2 and 3.

As described in Kallesøe et al., U.S. Pat. No. 5,487,756, and Hoffer et al., U.S. Pat. No. 5,824,027, both of which are incorporated herein by reference, a nerve cuff is typically a tubular structure having an outer wall which can be used to electrically isolate in vivo a tissue of interest, namely a nerve, inside a lumen defined by the cuff wall. Nerve cuffs which are designed to be chronically implanted are made from suitable biocompatible materials such as medical grades of silicone.

Nerve cuff 30 may be of any suitable design but as shown in these figures the preferred nerve cuff is a multichannel (ie. it has more than one electrode), multi-chambered nerve stimulation cuff. In a preferred embodiment the various apertures for electrodes 14 and catheters 25, if provided, may be cut in the cuff wall by a laser. The significance of catheters 25 is discussed below.

FIGS. 2 and 3 show the preferred nerve cuff of the present invention placed around a severed nerve in an amputated limb The preferred multichannel nerve cuff 30 has a closure comprising interdigitated tubular members 32 as described in Kallesøe et al. Nerve cuff 30 is closed by running a long member 31 through tubular members 32 when interdigitated.

As taught in the prior art, a plurality of electrodes 14 are placed within individual chambers 23 within nerve cuff 30. Chambers 23 are formed by ridges 24 extending into the lumen of nerve cuff 30. The chambers 23 serve to increase the selectivity of electrical stimulation directed to nerve 20 contained within cuff 30. Specifically, using multichannelled, multi-chambered nerve cuff 30, electrical signals provided by each of electrodes 14 are relatively isolated from one another and a signal from one electrode, or a certain set of electrodes, recruits only specific neurons to produce nervous signals (generally those neurons which are near the specific chamber which hosts the electrode providing the signal). In this manner, selective neurons can be recruited to produce nervous signals by providing signals through particular electrodes.

It will be appreciated that an amputee may appreciate different sensations depending upon which neurons are recruited to send a "sensory signal" If a neuron which had innervated the touch sensors on a fingertip is stimulated, for example, the amputee would have the sensation of this touch It has been determined by the present inventor that a plurality of signals may be generated by signal generator 12 and sent to electrodes 14, thereby stimulating various portions of nerve 20 The effect of this, when applied to amputees, is that phantom pain may be alleviated, since the provision of a regular flow of sensory information to the cerebral cortex, and the restoration of a balance of activity in large and small diameter sensory nerve fibers will tend to inhibit the exaggerated transmission of pain sensations to the sensory brain areas of the amputee.

It has also been discovered that certain patterns of stimulation, generally person-specific, will be more effective than others at alleviating phantom limb pain. In particular, patterns of signals approximating the train of signals received from a normal, innervated limb are have been discovered to be particularly effective. In a preferred embodiment of the present invention, the system may be programmed to optimize such stimulation patterns, or the choice of stimulation patterns may be controlled by the amputee. The amputee may adjust the amplitude and frequency of signals, for example, and also may select which channel (ie. electrode) transmits which signal.

In one method, the voltage, current and charge density per stimulation impulse is preferably in the range of 10-1000 μs in duration, preferably negative going if monophasic, preferably negative/positive if biphasic, and with current amplitude preferably in the range of 1-10 times the threshold current value for first recruitment of large-diameter sensory fibers, in order to not recruit pain fibers of smaller diameter and higher threshold Threshold can be determined by the lowest level of stimulation that is detected by the amputee as causing a sensation of cutaneous or proprioceptive modality Another way to determine the maximum stimulation to be used is by having the amputee report the highest level of stimulation that does not cause a noxious or painful sensation and keeping the stimulation safely below the threshold level for pain.

Further, the preferred method may provide the stimulation in trains in the range up to the maximum frequency that is perceived as non-fused tetani by the amputee, which could be as low as 10-20 Hz or as high as 300 Hz (300 impulses per second). The stimulation can be provided as a constant-frequency train, as regular bursts of constant frequency stimuli, as random bursts, as bursts of gradually increasing/decreasing frequency, or in many other patterns that are determined in part by the reported sensations elicited in the amputee and by the expressed preference of the amputee.

Again, while the electrical stimulation system of the present invention can be placed anywhere as long as the signals generated can be effectively transmitted to electrodes 14, in a preferred embodiment of the present invention, it is convenient to incorporate signal generator 12 within a prosthetic limb 40, as shown in FIG. 1. Prosthetic limb 40 may also be provided with a plurality of sensors 50 (the 3 sensors shown in FIG. 1 are labeled 50A, 50B and 50C), and various motors 60.

As described above, it has been found that the signals sent to nerve 20 to alleviate phantom limb pain are effective when they generally approximate the pattern and train of signals typically seen by the cortex as arising from a normal, innervated limb It is accordingly desirable to provide a stream of signals to nerve 20 which approximates the normal stream This can be effectively accomplished by "passing through" signals produced by sensors in the prosthetic limb 40 to nerve 20 Thus, the generator 12 can provide patterns of electrical stimulation to nerve 20 that depend upon, and approximate, the flow of information to generator 12 from sensors 50 in the prosthetic limb.

In a preferred embodiment, this may be accomplished by providing a microprocessor in conjunction with signal generator 12 which is programmed to accept signals produced by sensors 50, transducing them to be electrical signals sent to nerve 30 by signal generator 12. The sensory signals from sensors 50 may be telemetered directly from a transmitter in the prosthetic limb to a receiver (not shown) implanted in the stump, or the transduction may take place in a transducer and transmitter contained in the prostheses When the prosthetic limb 40 is in use, the sensory feedback system overrides and substitutes for the background activity from the phantom limb pain treatment stimulator described above, which would be switched on at other times (for example, when the amputee was asleep).

It will be appreciated that the sensory feedback system would operate most effectively if the signals sent to nerve 30 gave the "appropriate" sensation to the amputee upon the activation of a certain sensor in the prosthetic limb 40 For example, it is much preferred that an amputee get the sensation of a fingertip touching something if the touch sensor on a fingertip of the prosthetic limb 40 is stimulated, than some other sensation, although the cortex will over time adapt at least partially to "inaccurate" sensations The microprocessor can be programmed to send the appropriate signal to an appropriate electrode 14 depending upon the particular signal received from a sensor 50 This will simply require feed back from the amputee about what sensations are felt upon stimulation of different portions of nerve 30 (ie. different electrodes), and the appropriate matches programmed into the microprocessor.

In a further embodiment of the invention, if the system is equipped with a microprocessor, it may be programmed to monitor various voluntary command signals generated by the amputee together with the sensory information flow arriving from sensors 50 in the prosthetic limb 40 and may thus control the action of the motors 60 placed in the prosthetic limb 40 that control the position and movement of the prosthetic limb joints and digits.

In operation, where the goal is to provide sensory feedback—arising from the prosthetic limb, stimulation preferably will be applied continuously during those periods when the prosthetic limb 40 is connected and in use. When not in use, stimulation may still be applied by signal generator 12 to provide cortical stimulation to keep pain sensation from being interpreted by amputee.

The stimulation will preferably be linked to the intensity of a given sensory input that is being monitored by sensors in the prosthetic limb For example, for one channel of feedback the monitored input could be grip force, or pressure between the thumb and forefinger In such case, the intensity of stimulation of the nerve would be graded, within the available dynamic range, to the range of intensities to be monitored For example if grip force in the range 0-10 N is to be monitored and the dynamic range of stimulation frequencies detected by the amputee is 0-20 Hz, then the stimulation could be scaled so that every 1 Hz increment represents an increase of 0.5 N and the stimulation frequency range 0-20 Hz represents the grip force range 0-10 N.

For multi-channel systems, essentially similar patterns may be employed, but these can be provided independently to each channel, in such a way that all the stimulation parameters may be different and independently controlled for each channel, and each channel can be dedicated to represent a different sensory modality. For example, if four sensory channels are available for feedback from a hand prosthesis, these can be assigned to represent grip force in the thumb, slip detection in the thumb, angle of the wrist joint, and heat sensed in the palm of the hand. Each of the four sensory inputs would be provided by appropriate sensors built into the prosthetic hand and wrist and would be coded independently as described above for single-channel feedback systems.

It is believed that the systems of the present invention should be implanted as soon as possible following limb amputation (or even before) to provide the greatest benefit, so as to maximally arrest cortical changes subsequent to amputation.

As will be apparent to those skilled in the art in the light of the foregoing disclosure, many alterations and modifications are possible in the practice of this invention without departing from the spirit or scope thereof. For example, it is not critical to the invention to have the electrical signals produced by a signal generator be transmitted to nerve 20 electrically. The nerve cuff 30 may support the mechanical anchoring of one or more signal transducers, their associated conductors and associated signal processing units. For example, it may be appropriate to have an electrochemical, pharmacological and/or optical system to transduce signals from the signal generator 12 to recruit neurons in nerve 30. Such a pharmacological system 70, which includes catheters 25, is also shown in FIG. 1.

Further, while the system described herein is described with particular application to amputees, it may also suitably be employed with appropriate modification to work in subjects with other peripheral nerve injuries other than those caused by amputation.

Accordingly, the scope of the invention is to be construed in accordance with the substance defined by the following claims.

What is claimed is:

1. A prosthetic system for a patient having a limb stump, comprising:
a prosthetic limb that is attachable to the patient's limb stump, the prosthetic limb including a plurality of sensors that produce sensory signals;
a signal generator for producing electrical stimulation signals to stimulate one or more selected sensory nerve fibers of a severed limb nerve, the electrical stimulation signals approximating a pattern of sensations that would be received from a normal, innervated limb before it was amputated;
a microprocessor that receives the sensory signals and is programmed to cause the signal generator to produce the electrical stimulation signals and to deliver the electrical stimulation signals to the one or more selected sensory nerve fibers in order to provide sensations to the patient that appear to arrive from the prosthetic limb, wherein the selection of the one or more sensory nerve fibers is based on feedback from the patient regarding which sensory nerve fibers correspond to which of the plurality of sensors, the microprocessor being programmed to cause the signal generator to produce electrical stimulation signals in the absence of sensory signals produced by the plurality of sensors in order to alleviate phantom limb pain;
means for transmitting the sensory signals from the plurality of sensors to the microprocessor; and
means for transmitting the electrical stimulation signals to the selected sensory nerve fibers;
wherein the means for transmitting the electrical stimulation signals to the selected sensory nerve fibers includes a plurality of electrodes adapted for implantation in close proximity to the severed limb nerve and wherein each electrode is in close proximity to different sensory nerve fibers of the severed limb nerve.

2. The system of claim 1, wherein the selection of the electrical stimulation signals is based on feedback from the patient.

3. The system of claim 1, wherein the signal generator and microprocessor are adapted for location outside the body.

4. The system of claim 1, wherein the signal generator and microprocessor are adapted for location inside the prosthetic limb.

5. The system of claim 1, wherein the signal generator and microprocessor are adapted for location inside the body.

6. The system of claim 1, wherein the signal generator and microprocessor are adapted for location inside the limb stump.

7. The system of claim 1, wherein the plurality of sensors sense any of touch, pressure, force, slip, joint position or temperature.

8. The system of claim 1, wherein the means for transmitting the electrical stimulation signals is telemetric.

9. The system of claim 8, wherein the telemetric transmission means includes a transmitting antenna coupled to the signal generator and a receiving antenna coupled to the electrodes.

10. The system of claim 1, wherein the means for transmitting the electrical stimulation signals includes cables extending between the one or more electrodes and the signal generator.

11. The system of claim 1, wherein the electrical stimulation signals are monophasic.

12. The system of claim 11, wherein the monophasic electrical stimulation signals are negative going.

13. The system of claim 1, wherein the electrical stimulation signals are biphasic.

14. The system of claim 13, wherein the biphasic electrical stimulation signals are negative/positive going.

15. The system of claim 1, wherein the signal generator can adjust the amplitude of the electrical stimulation signals.

16. The system of claim 1, wherein the signal generator can adjust the frequency of the electrical stimulation signals.

17. The system of claim 1, wherein the electrodes are incorporated within an insulating nerve cuff that when implanted, circumferentially surrounds the severed limb nerve, wherein each electrode in the nerve cuff is in close proximity to different sensory nerve fibers of the severed limb nerve.

18. The system of claim 17, wherein the nerve cuff is a multichambered, tubular nerve cuff including a number of parallel ridges that provide insulation between electrodes.

19. The system of claim 1, further comprising a nerve cuff that when implanted surrounds the severed limb nerve, the nerve cuff having a number of isolated chambers and a catheter associated with each chamber for selectively delivering pharmacological agents to sensory nerve fibers of the severed limb nerve and wherein the means for delivering the electrical stimulation signals to the selected nerve fibers causes a pharmacological agent to be delivered in one or more of the catheters.

20. The system of claim 1, wherein the means for transmitting the electrical stimulation signals to the sensory nerve fibers in the limb stump include an optical transmission link.

21. The system of claim 1, wherein the electrical stimulation signals are in the form of impulses having a duration in the range of about 10 to 1000 µs and a current amplitude selected to be 1-10 times a current threshold required to recruit a large diameter sensory nerve fiber without recruiting a pain nerve fiber.

22. A system for alleviating phantom limb pain of a patient having a limb stump, comprising:
- a signal generator for producing electrical stimulation signals to stimulate one or more selected sensory nerve fibers of a severed limb nerve, the electrical stimulation signals being in the form of impulses having a duration in the range of about 10 to 1000 µs and a current amplitude selected to be 1-10 times a current threshold required to recruit a large diameter sensory nerve fiber without recruiting a pain nerve fiber, and approximating a pattern of sensations that would be received from a normal, innervated limb before it was amputated;
- a microprocessor that is programmed to cause the signal generator to produce the electrical stimulation signals and to deliver the electrical stimulation signals to one or more selected sensory nerve fibers in order to alleviate phantom limb pain, wherein the selection of the electrical stimulation signals is based on feedback from the patient; and
- means for transmitting the electrical stimulation signals to the selected sensory nerve fibers;
- wherein the means for transmitting the electrical stimulation signals to the selected sensory nerve fibers includes a plurality of electrodes adapted for implantation in close proximity to the severed limb nerve and wherein each electrode is in close proximity to different sensory nerve fibers of the severed limb nerve.

23. The system of claim 22, wherein the signal generator and microprocessor are adapted for location outside the body.

24. The system of claim 22, wherein the signal generator and microprocessor are adapted for location inside the body.

25. The system of claim 22, wherein the signal generator and microprocessor are adapted for location inside the limb stump.

26. The system of claim 22, wherein the means for transmitting the electrical stimulation signals is telemetric.

27. The system of claim 26, wherein the telemetric transmission means includes a transmitting antenna coupled to the signal generator and a receiving antenna coupled to the electrodes.

28. The system of claim 22, wherein the means for transmitting the electrical stimulation signals includes cables extending between the one or more electrodes and the signal generator.

29. The system of claim 22, wherein the electrical stimulation signals are monophasic.

30. The system of claim 29, wherein the monophasic electrical stimulation signals are negative going.

31. The system of claim 22, wherein the electrical stimulation signals are biphasic.

32. The system of claim 31, wherein the biphasic electrical stimulation signals are negative/positive going.

33. The system of claim 22, wherein the signal generator can adjust the amplitude of the electrical stimulation signals.

34. The system of claim 22, wherein the signal generator can adjust the frequency of the electrical stimulation signals.

35. The system of claim 22, wherein the electrodes are incorporated within an insulating nerve cuff that when implanted, circumferentially surrounds the severed limb nerve, wherein each electrode in the nerve cuff is in close proximity to different sensory nerve fibers of the severed limb nerve.

36. The system of claim 35, wherein the nerve cuff is a multichambered, tubular nerve cuff including a number of parallel ridges that provide insulation between electrodes.

37. The system of claim 22, further comprising a nerve cuff that when implanted surrounds the severed limb nerve, the nerve cuff having a number of isolated chambers and a catheter associated with each chamber for selectively delivering pharmacological agents to sensory nerve fibers of the severed limb nerve and wherein the means for delivering the electrical stimulation signals to the selected nerve fibers causes a pharmacological agent to be delivered in one or more of the catheters.

38. The system of claim 22, wherein the means for transmitting the electrical stimulation signals to the sensory nerve fibers in the limb stump include an optical transmission link.

39. A method of alleviating phantom limb pain and providing sensory feedback to a patient having a limb stump, comprising the steps of:
- providing the patient with a prosthetic limb that is attachable to the patient's limb stump, the prosthetic limb including a plurality of sensors that produce sensory signals;
- processing the sensory signals produced by the plurality of sensors;
- generating electrical stimulation signals approximating a pattern of sensations that would be received from a normal, innervated limb before it was amputated, in response to the processed sensory signals;
- generating electrical stimulation signals in the absence of sensory signals produced by the plurality of sensors to alleviate phantom limb pain in the absence of sensory signals; and
- delivering the electrical stimulation signals to the one or more selected sensory nerve fibers in order to provide sensations to the patient that appear to arrive from the prosthetic limb, wherein the selection of the one or more sensory nerve fibers is based on feedback from the patient regarding which sensory nerve fibers correspond to which of the plurality of sensors.

40. The method of claim 39, wherein the selection of the electrical stimulation signals is based on feedback from the patient.

41. The method of claim 39, wherein the plurality of sensors sense any of touch, pressure, force, slip, joint position or temperature.

42. The method of claim 39, wherein the electrical stimulation signals are monophasic.

43. The method of claim 42, wherein the monophasic electrical stimulation signals are negative going.

44. The method of claim 39, wherein the electrical stimulation signals are biphasic.

45. The method of claim 44, wherein the biphasic electrical stimulation signals are negative/positive going.

46. The method of claim 39, further comprising the step of adjusting the amplitude of the electrical stimulation signals.

47. The method of claim 39, further comprising the step of adjusting the frequency of the electrical stimulation signals.

48. The method of claim 39, wherein the electrical stimulation signals are in the form of impulses having a duration in the range of about 10 to 1000 µs and a current amplitude selected to be 1-10 times a current threshold required to recruit a large diameter sensory nerve fiber without recruiting a pain nerve fiber, the electrical stimulation signals.

49. A prosthetic limb for a patient having a limb stump to be used in combination with means for transmitting electrical stimulation signals to the selected sensory nerve fibers including a plurality of electrodes adapted for implantation in close proximity to the severed limb nerve and wherein each electrode is in close proximity to different sensory nerve fibers of the severed limb nerve, the prosthetic limb comprising:

a plurality of sensors that produce sensory signals;

a signal generator for producing electrical stimulation signals to stimulate one or more selected sensory nerve fibers of a severed limb nerve, the electrical stimulation signals approximating a pattern of sensations that would be received from a normal, innervated limb before it was amputated;

a microprocessor that receives the sensory signals and is programmed to cause the signal generator to produce the electrical stimulation signals and to deliver the electrical stimulation signals to the one or more selected sensory nerve fibers in order to provide sensations to the patient that appear to arrive from the prosthetic limb, wherein the selection of the one or more sensory nerve fibers is based on feedback from the patient regarding which sensory nerve fibers correspond to which of the plurality of sensors, the microprocessor being programmed to cause the signal generator to produce electrical stimulation signals in the absence of sensory signals produced by the plurality of sensors in order to alleviate phantom limb pain; and means for transmitting the sensory signals from the plurality of sensors to the microprocessor.

\* \* \* \* \*